United States Patent
Fava et al.

(10) Patent No.: US 6,721,615 B2
(45) Date of Patent: Apr. 13, 2004

(54) METHOD FOR THE MANAGEMENT OF WORKCELL SYSTEMS BASED ON AN AUTOMATION MANAGEMENT SYSTEM

(75) Inventors: Daniele Fava, Milan (IT); Elisabetta Garghentino, Milan (IT); Gianandrea Pedrazzini, Segrate (IT)

(73) Assignee: INPECO s.r.l., Segrate (IT)

( * ) Notice: Subject to any disclaimer, the term of this patent is extended or adjusted under 35 U.S.C. 154(b) by 72 days.

(21) Appl. No.: 10/113,575

(22) Filed: Apr. 2, 2002

(65) Prior Publication Data

US 2002/0147515 A1 Oct. 10, 2002

(30) Foreign Application Priority Data

Apr. 5, 2001 (EP) ............................................ 01830237

(51) Int. Cl.⁷ ........................... G06F 19/04; G05B 11/01
(52) U.S. Cl. ........................... 700/99; 718/104; 718/105
(58) Field of Search ........................ 700/11, 95, 99–101, 700/104, 112, 245–247, 257, 266; 422/63–67; 718/104, 105

(56) References Cited

U.S. PATENT DOCUMENTS

| | | | |
|---|---|---|---|
| 5,093,794 A | 3/1992 | Howie et al. | 364/468 |
| 5,282,149 A | 1/1994 | Grandone et al. | 364/497 |
| 5,619,428 A * | 4/1997 | Lee et al. | 364/551.01 |
| 5,846,491 A * | 12/1998 | Choperena et al. | 422/67 |
| 6,022,746 A | 2/2000 | Fritchie et al. | 436/50 |
| 6,208,904 B1 * | 3/2001 | Mullen, Jr. | 700/9 |
| 6,594,537 B1 * | 7/2003 | Bernstein et al. | 700/100 |

FOREIGN PATENT DOCUMENTS

| | | |
|---|---|---|
| EP | 0240134 A2 | 10/1987 |
| EP | 0596205 A2 | 5/1994 |
| EP | 0633207 A1 | 1/1995 |
| WO | WO94/11838 | 5/1994 |
| WO | WO01/09618 | 2/2001 |

OTHER PUBLICATIONS

Lindsey et al, Chem & Intell Lab Systems . . . 21, 1993, pp. 139–150, Toward high performance parallel experimentation . . .

* cited by examiner

Primary Examiner—Leo Picard
Assistant Examiner—Sean P Shechtman
(74) Attorney, Agent, or Firm—Jacobson Holman PPC (57) ABSTRACT

A method for the management of a Workcell System capable to control concurrent processes that use pieces of equipment, here called Resources, interacting with each other according to the needs and the changes that have not been forecast in advance in their process cycles, by means of a continuous real-time re-scheduling of automatic tasks. According to an embodiment, the method for the management of Workcell Systems, using an Automation Management System to control a plurality of Resources, designated to handle Samples along the Workcell Systems to perform operations on the Samples, includes associating a Sample Protocol to each Sample, associating to each Resource a Resource Driver, controlling the Resource Drivers by a Process Controller which communicates with the Resource Drivers by means of variables associated to each Resource, executing the Sample Protocols by the Process Controller in a concurrent way, and automatically modifying the Sample Protocols by continuously re-scheduling automatic tasks on different Resources, according to the results of the execution of the Sample Protocols and the status of the Resources, as indicated by the status of the variables, and thus obtaining an intelligent and reactive control of the workflow, automatically and dynamically taking the appropriate decisions.

22 Claims, 5 Drawing Sheets

METHOD FOR THE MANAGEMENT OF WORKCELL SYSTEMS BASED ON AN AUTOMATION MANAGEMENT SYSTEM

BACKGROUND OF THE INVENTION

1. Field of the Invention

The present invention relates to a method for the management of Workcell Systems capable to control concurrent processes that use pieces of equipment, here called Resources, interacting with each other according to the needs and the changes that have not been forecast in advance in their process cycles, by means of a continuous real-time re-scheduling of automatic tasks. Further it relates to an Automation Management System.

2. Description of the Related Art

Robotic systems are often used to increase productivity, reduce production costs, eliminate human errors, remove human Operators from a dangerous environment or simply to take over boring and frustrating tasks.

This is the case of the automation of industrial production processes where the use of electromechanical devices has been exploited for the execution of repetitive and, sometimes, complex tasks. The automation concept has been limited to cycles that might be interrupted waiting for the coincidence with other tasks but never with a continuous re-scheduling of tasks depending on circumstances that are not, and cannot be, forecast in advance.

Moreover, the automation concept has been limited, so far, to production processes where pieces of equipment are dedicated to specific tasks, notwithstanding if they were saturated or not, and without any attempt to use them to perform concurrent processes, or to take any automatic decision, based on expert-system rules, to re-do some process steps or to schedule new process tasks according to rules applied to the results achieved by the System and/or to unexpected Operator requests.

Thus, prior art automation concepts cannot be applied to environments where the tasks can be changed very often as, for example, the ones of Laboratory Medicine and Research Laboratories, that are distinguished by: unpredictable environment, use of general purpose instruments that may be used for different assays, small scale automation, need of flexible automation, need to saturate complex and expensive equipment that are generally used for different protocols that need to be run almost contemporaneously, need to give the automated system the possibility to automatically modify the sample protocols upon User request and/or expert-system rules based on the results of the assay process.

SUMMARY OF THE INVENTION

It is an object of the present invention to overcome the above said limit and to make possible the contemporaneous execution of concurrent processes that make use of common pieces of equipment in order to obtain their better saturation and to give the possibility to automate processes with dynamic data entry and/or continuous request reception.

According to the present invention, these and other objects are attained by means of a method for the management of Workcell Systems, using an Automation Management System to control a plurality of Resources, designated to handle Samples along said Workcell Systems to perform operations on said Samples, comprises the following steps: associating a Sample Protocol to each Sample, associating to each Resource a Resource Driver, capable to drive said Resource, each of said Resource Driver is controlled by a Process Controller and communicates with the other Resource Drivers by means of variables associated to each Resource, which define and modify the status of said Resources, executing said Sample Protocols by said Process Controller in a concurrent way, guaranteeing multi-threading, bottleneck avoidance, dynamic assignment of Resources in mutual exclusion, sample priority handling, Resource load balancing and automatic error recovery, automatically modifying said Sample Protocols by continuously re-scheduling automatic tasks on different Resources, according to the results of the execution of said Sample Protocols and the status of said variables, expressing the status of said Resources, and thus having an intelligent and reactive control of the workflow, automatically and dynamically taking the appropriate decisions.

Whereas a Sample is a specimen of material in a form that allows treatment or assay on the appropriate Resources, and a Sample Protocol is a collection of data indicating the tasks that have to be executed on the associated Sample in said Workcell System.

For such reasons the invention has been dedicated to the automation of Laboratory Protocols but can be applied to industrial automation, at the moment the complexity of industrial processes reaches the same complexity level as Laboratory environments.

BRIEF DESCRIPTION OF THE DRAWINGS

The features and the advantages of the present invention will be evident from the following detailed description of embodiments thereof, illustrated as non-limiting examples in the annexed drawings, wherein.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
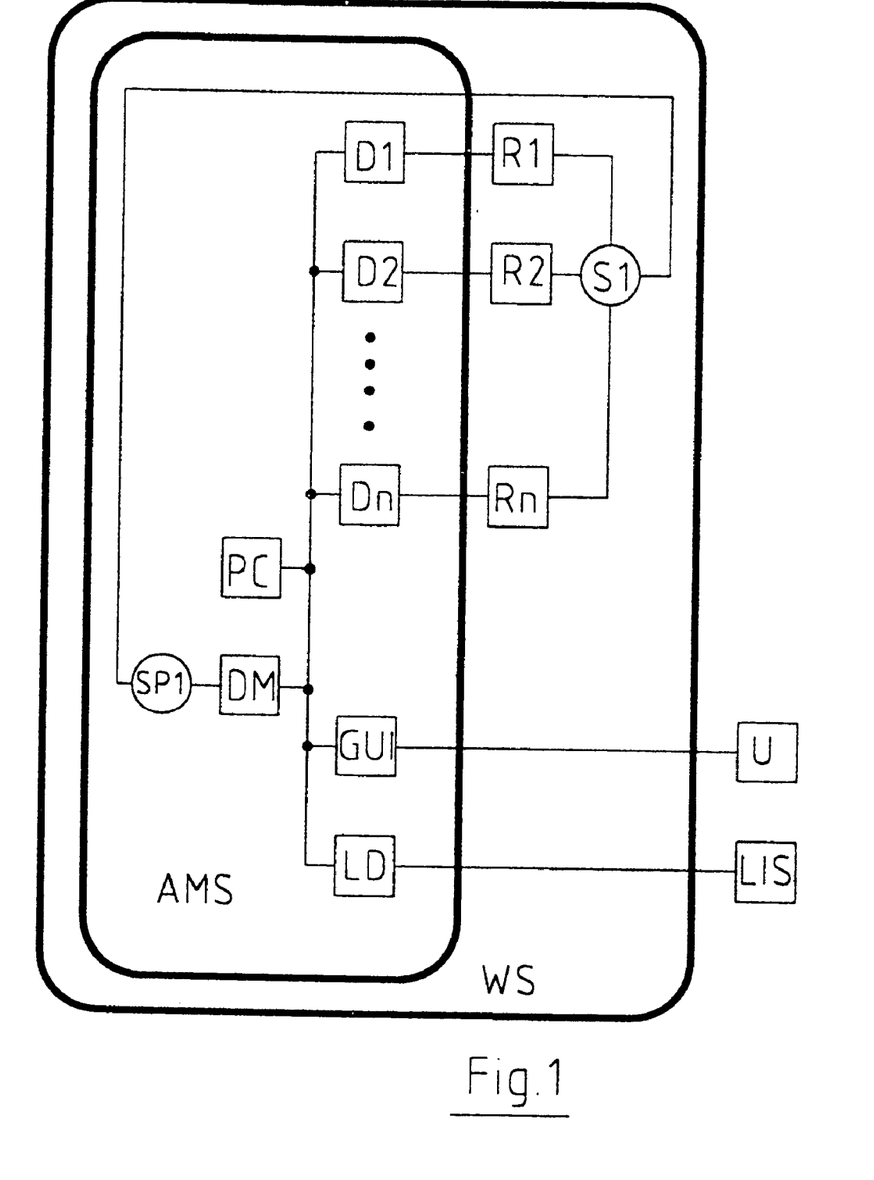
FIG. 1 shows a general structure of a Workcell System designed according to the present invention.

Referring now to FIG. 1, where is represented a general structure of a Workcell System, R1, R2, . . . Rn represent the various Resources, D1, D2, . . . Dn the associated Resource Drivers, S1 a generic Sample and SP1 the associated Sample Protocol, PC represents the Process Controller, DM the Data Manager, LIS the Laboratory Information System, LD the Laboratory Information System Driver, U the User or human Operator, GUI the Graphic User Interface, AMS the Automation Managing System and WS the Workcell System itself.

Figure 1A:
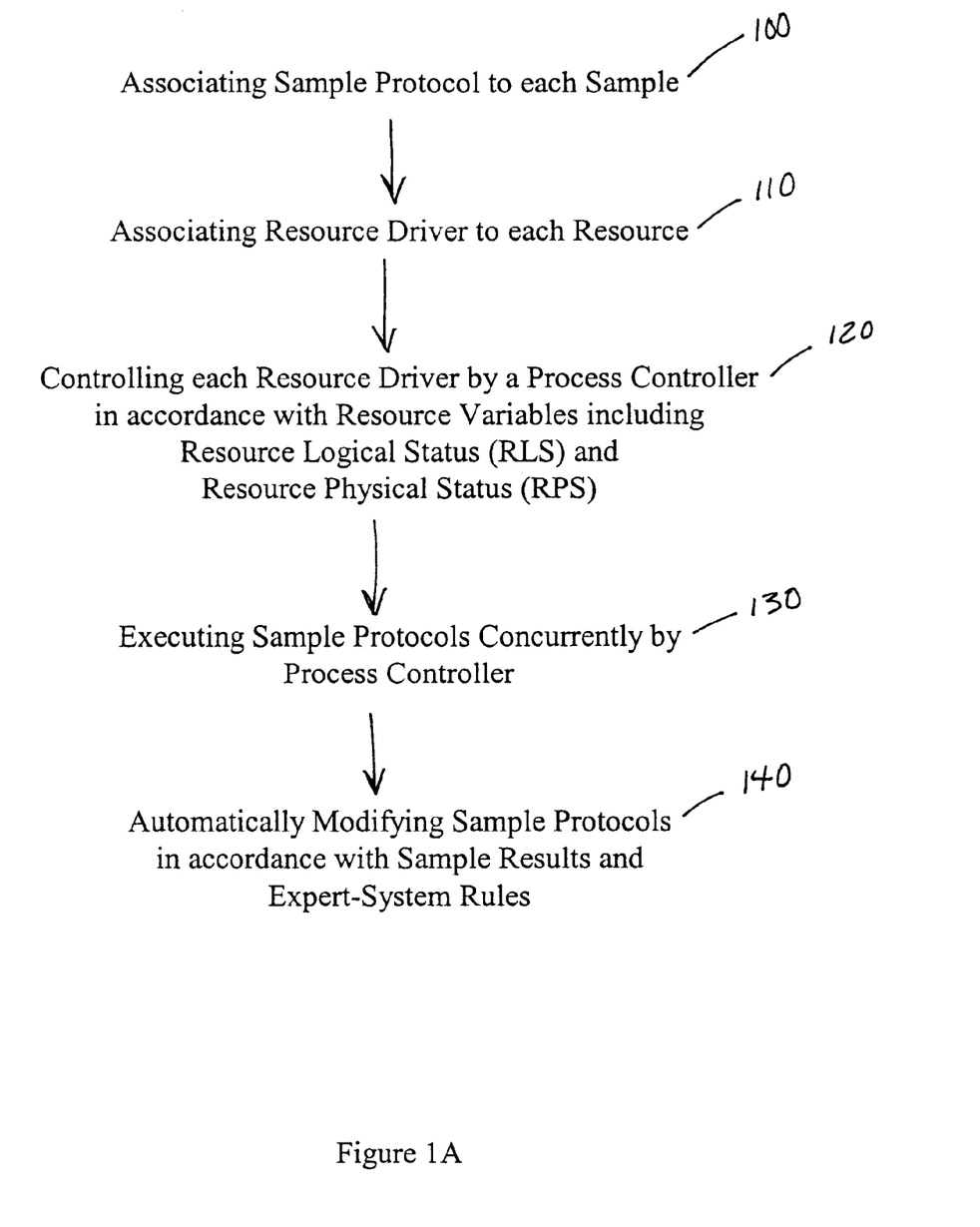
FIG. 1A is a flowchart summarizing the method for the management of Workcell Systems, in accordance with the present invention.

The method for the management of Workcell Systems, using an Automation Management System to control a plurality of Resources, designated to handle Samples along said Workcell Systems to perform operations on the Samples, is summarized in FIG. 1A and includes the steps of associating a Sample Protocol to each Sample, step 100, and associating to each Resource a Resource Driver capable to drive the Resource, step 110. Each of the Resource Drivers is controlled by a Process Controller, step 120, which Process Controller communicates with the Resource Drivers by means of variables associated to each Resource; the variables define and modify the status of the Resources and may include RLS (Resource Logical Status) and RPS (Resource Physical Status). The Process Controller executes the Sample Protocols in a concurrent way, step 130, guaranteeing multi-threading, bottleneck avoidance, dynamic assignment of Resources in mutual exclusion, sample priority handling, Resource load balancing and automatic error recovery. The Sample Protocols are automatically modified, step 140, by continuously re-scheduling automatic tasks on different Resources, according to the results of the execution of the Sample Protocols and the status of the Resources, as indicated by the status of the variables, such that an intelligent and reactive workflow control process, automatically and dynamically taking the appropriate decisions, is performed.

The working of the Workcell System of FIG. 1 will be explained in the following exemplifying embodiments.

Figure 2:
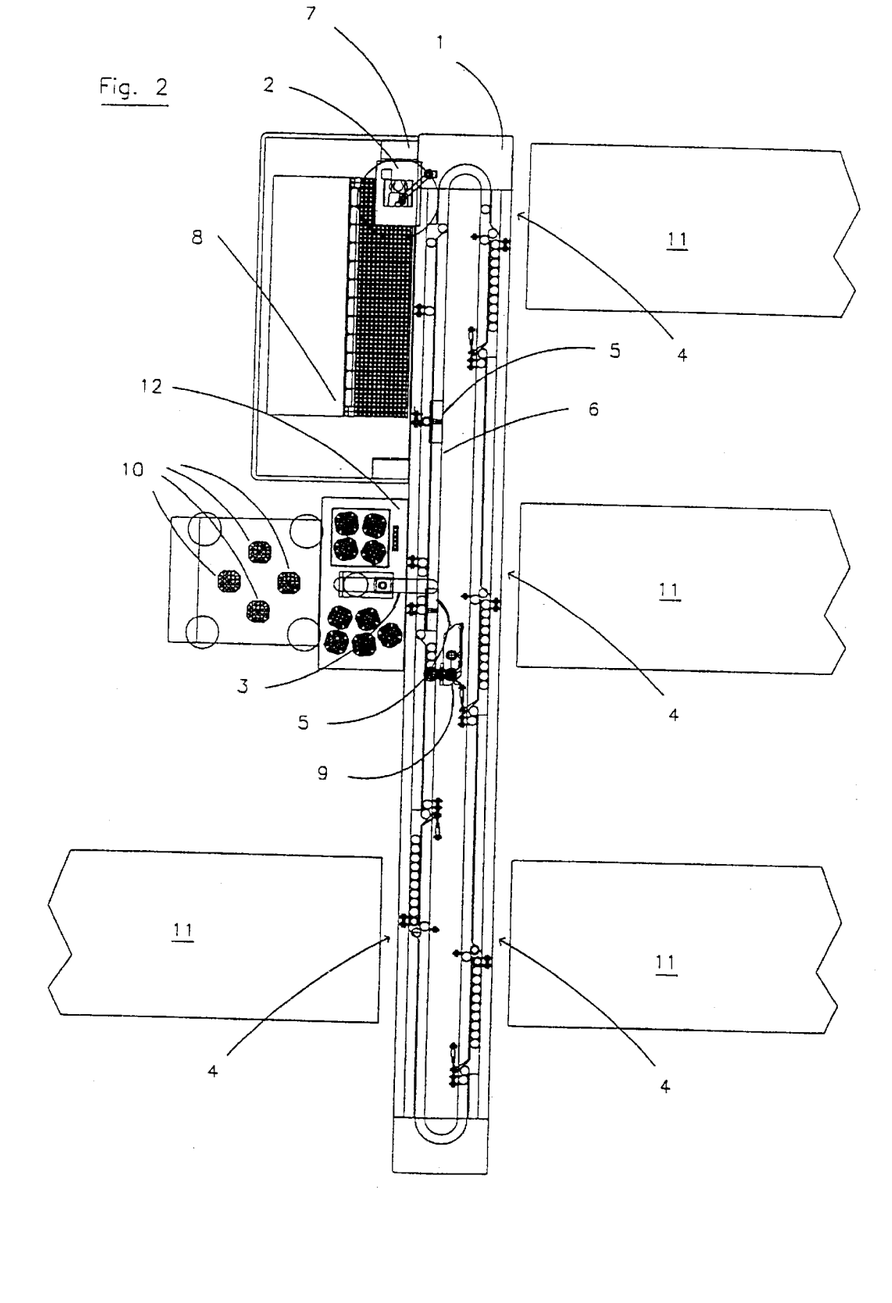
FIG. 2 shows a layout of an In Vitro Diagnostics Laboratory Automation Workcell System.

An Example of In Vitro Diagnostics Laboratory Automation Workcell System (IVD LAWS) is shown in FIG. 2, and integrates as Sample Containers: sample tubes containing a biological fluid (e.g. blood or any other material), sample racks carrying, for example, 12, 20 or 48 sample tubes each, and the following pieces of equipment as Resources: Sample Carrier Devices: an Inpeco Transport and Positioning Module (TPM) 1, i.e. a belt conveyor system transporting Pallets (i.e. single sample carriers) containing Sample Tubes (each Pallet is identified by a radio-frequency transponder, appropriately read from time to time by radio frequency devices integrated in a Transponder Tag Reading System), an Input/Output Module (IOM) polar robot 2 mounted on an Inpeco air-bearing track to move samples from/to the Input/Output area to/from the TPM, a Centrifuge Module (CM) polar robot 3 to move samples from/to the Centrifuge area to/from the TPM, one or more robotic systems 4 to interface the Sample Assay Device Analyser with the TPM.

The same example integrates as Sample Container Handling Devices: two Datalogic barcode readers 5 for Sample Container identification, an Input/Output area 6 equipped with sensors and actuators to detect and lock A sample racks, a Vision System 7 to recognise sample racks and sample tubes, two Sample Container Detection Devices 8 to identify sample tube height and diameter, a Decapper System 9 to remove sample closures (caps) from sample tubes as necessary, Sample Treatment Devices: a Hettich Rotanta Centrifuge 10 for sample centrifugation, and as Sample Assay Devices: up to ten different Clinical-Chemistry, Immunochemistry, or other Diagnostics Analysers 11, and a Sartorius BP6100 Balance Scale 12 to measure sample weights.

The state of the art provides for systems that perform Laboratory Diagnostics analyses foresees either the manual execution of the pre-analytical tasks (i.e. sample identification, centrifugation, decapping, loading of samples into the Analysers) and post-analytical tasks (i.e. unloading of samples from the Analysers, sample sorting, test re-execution in case of errors, new analysis requests due to particular rules), or the automatic execution of the pre-analytical phase only, but in a sequential fashion, without the handling of priorities and concurrency.

On the contrary, thanks to the present invention, the In Vitro Diagnostics Laboratory Automation Workcell System that uses the Laboratory Automation Management System, automates all the pre-analytical, analytical and post-analytical phases of Sample assaying in a homogeneous, concurrent, reactive, dynamic and expert-system-rule-based fashion.

The only manual tasks to be performed by the Operator are loading and unloading Sample Racks, containing barcode-labelled sample tubes, that arrive from the Hospital blood draw area or from other clinical locations. After the Operator loads the racks into the LAWS Input/Output area 6, the Workcell System automatically senses and locks the racks, and the IOM Robot takes a picture of each rack by a digital camera 7, identifying the sample tubes contained in the rack and the rack ID (and consequently the area where the sample was collected or eventually the phlebotomist who performed the collection).

Then, the IOM robot 2 automatically picks up the tubes from the racks and puts them into the TPM 1, where the Barcode Reader 5 and the Sample Container Detection Device 8 detect the Sample Container ID and its dimension (height and diameter). The Sample Container ID is associated with the proper Sample Protocol (i.e. the test orders) downloaded by the Laboratory Information System (or manually inserted by the Operator using the Graphic User Interface as necessary) and the proper pallet ID, in order to trace the Sample Container along the TPM 1. Depending upon the Sample Protocol, the Sample is centrifuged as necessary (in this phase, the sample quantity is measured by the Balance Scale 12 in order to know if the sample is sufficient to perform the analyses, and to load the Sample Containers into the Centrifuge 10 in a balanced way: a balancing algorithm is used in this respect), and decapped as necessary by the Decapper System 9 (i.e. the Sample Container closure is removed—it is possible also to load pre-centrifuged or pre-decapped Sample Containers in particular Input locations, and these tubes will be treated by the System accordingly).

Then, the Sample Containers are automatically routed to the appropriate Analysers 11, where the appropriate tests are performed. Each Analyser 11 is handled by two Resource Drivers, the first one managing the Laboratory Information System (LIS) data communication, i.e. the transmission of the test orders and the reception of sample results and/or analytical errors after the assays are performed, the second one managing the Laboratory Automation System (LAS) communication, i.e. the management of the robotic automation commands that actually load the Sample into the analyser.

After all the analyses have been performed, the Sample Container is moved into the appropriate sorting rack (depending on the test request that have to be eventually executed in other off-line Analysers), and, when all the test results are received (and eventually some derived results are mathematically calculated), the LAWS Process Controller (the co-ordinator of Resource drivers) takes a decision, depending on the results and the configured expert-system rules, to release the results to the Laboratory Information System or to ask the Operator intervention to validate the results. Eventually, the Data Manager (the handler of the Sample Protocol database) may automatically ask for new test orders to be added to the Sample Protocol, or to automatically re-execute some tests and/or add some new tests (called reflex tests) to the Sample Protocol for further analytical investigation (in this cases, the Sample Container is automatically picked up again by the IOM Robot 2 and routed to the appropriate Analysers 11 accordingly— provided that the Sample quantity is estimated as sufficient to complete the newly requested analyses).

Thanks to the present invention it is possible to co-ordinate all the Resources of the System in a multi-tasking/multi-threading fashion, and thus allowing each Sample Container to have a different treatment based on Sample Protocol priority, Sample and Sample Container characteristics (i.e. whether the sample must be centrifuged or not, or whether the sample container has the closure or not, or sample container height, diameter and weight), Sample Protocol tests to be executed (tests may be executed on different Analysers, and Sample Containers may be sorted to different output racks according to tests that are left for Analysers that are located outside the Laboratory Automation Workcell System), and test results that may cause new test requests.

Some critical resources, like the Input/Output area 6, the Centrifuge 10, or some Analyser 11 buffers (i.e. waiting queues of Pallets containing Samples to be assayed in those Analysers), that can cause system bottlenecks, are handled with User-configurable expert-system-based rules, which allow the Process Controller to have an intelligent control of the workload balancing flow, taking the appropriate decisions on the Sample Container routing.

For instance, the system automatically estimates the time before completion of each Sample test, and then it distributes Sample Containers along the System in order to optimise the workflow, avoiding queues and bottlenecks. Also, if a Resource is off-line or busy (e.g. an Analyser), some tasks that were scheduled for that Resource are automatically rescheduled for a different resource (e.g. another equivalent Analyser), maximising efficiency and throughput. Also, depending on User request or event-driven re-scheduling algorithms, the assaying process is distributed along the equivalent Analysers in order to minimise the splitting of test requests (i.e. the loading of Samples in different equivalent Analysers), or to get fastest results (thus decreasing the average turn-around-time of results), or to minimise instruments (e.g. during the night period, where only few samples must be executed), or to get the best test fit in Analysers (in order to have the best throughput), or according to other rules.

The User can access the Graphic User interface to modify the configuration parameters and the rules to handle automatic test re-execution, reflex testing, and mathematical calculation of derived results, or to view test results and eventually validate or schedule a re-execution of the tests that the internal LAWS Data Manager expert system does not handle automatically, or for diagnostics and trouble-shooting reasons.

The communication between the Process Controller and each Resource Driver is achieved via a set of variables called RLS (Resource Logical Status) and RPS (Resource Physical Status).

The RLS variable indicates the status of the current task execution of the relevant Resource, i.e. it may be Ready if the Resource is ready to execute new tasks, Busy if it is busy executing a task and thus it cannot currently receive new commands, Error if it is in error state, Task End if it has terminated its current task and it is waiting that the Process Controller updates the RPS variables, etc.

The RPS variables indicate the physical status of a Resource, e.g. for an Analyser, the RPS is a set of variables indicating the current menu of the Analyser itself (i.e. the list of all available calibrated reagents to perform the tests), the available consumables (i.e. tips, aliquots, cuvettes, etc.) and the current Analyser workload (i.e. the number of tests being currently performed, the estimated average time for completion, the number of scheduled tests to be run, etc.).

The Process Controller, depending upon the RLS and the RPS variables of the various Resources, and upon the Sample Protocols of the Samples being currently in process on the Workcell System, automatically decides, step by step, where and when to execute sample treatment (e.g. centrifuging), sample container handling (i.e. decapping) and sample assaying (i.e. executing some of all tests on the relevant samples).

Figure 3:
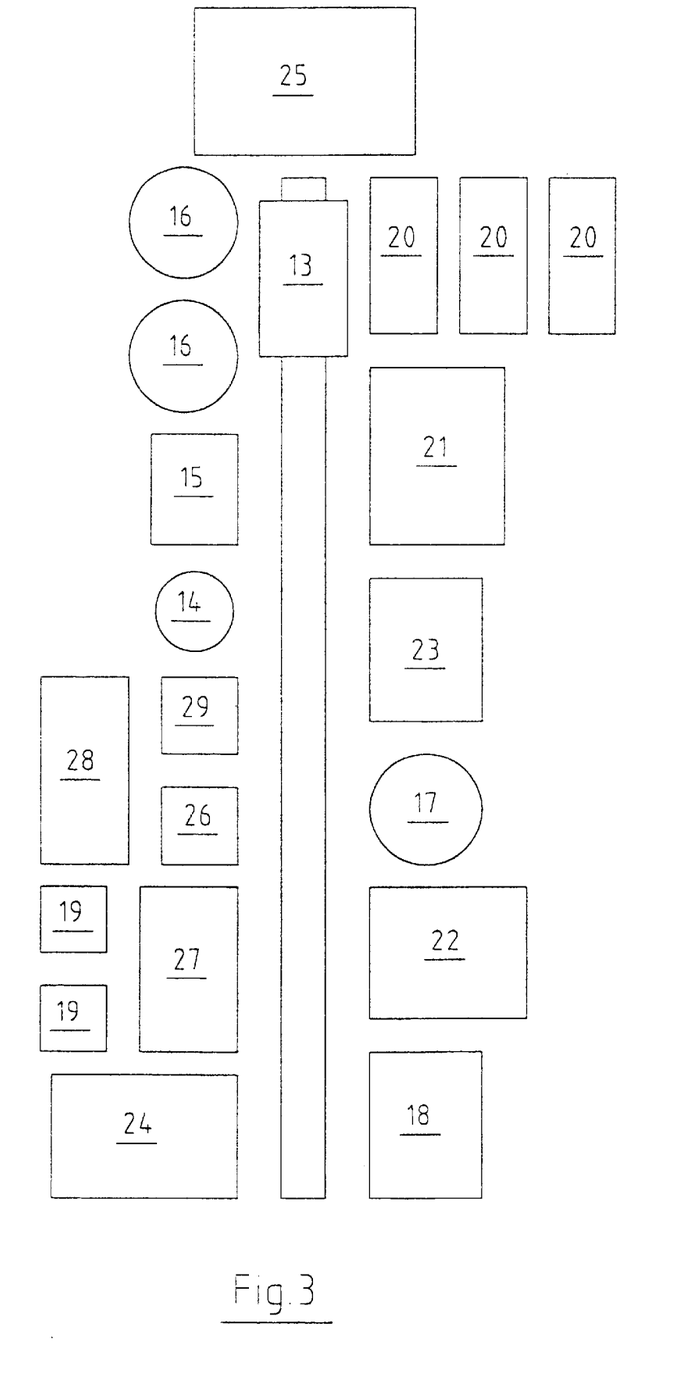
FIG. 3 shows the layout of a High Throughput Screening or Nucleic Acid Technology Laboratory Automation Workcell System.

An Example of High Throughput Screening Laboratory Automation Workcell System (HTS LAWS) or Nucleic Acid Technology Laboratory Automation Workcell System (NAT LAWS), using the Method of the present invention, shown in FIG. 3, integrates as Sample Containers: Microtiter Plates (plates containing a multiple number of Samples, located in portions of the Plate called wells), Tip Racks (containers of tips, that are used by some Resources to move part of a Sample to and from the Sample Container, and Sample Tubes), and the following pieces of equipment as Resources: Sample Carrier Devices: CRS Robotics A255 articulated robot 13 mounted on a 4.5 meter long Inpeco TR-10/4 air bearing track (a double pair of pincers are designed to transfer Microtiter plates and Tip Racks and Sample Tubes to and from all Resources in the LAWS), and a Turntable 14 (for plate rotation).

The same example integrates Sample Container Handling Devices: a MicroScan Raster barcode reader 15 for Sample Container identification, two Plate Storage Carousels 16 that can accommodate 144 Microtiter Plates each, one Tip Rack Storage Carousel 17, which can accommodate 72 tip racks or deep well plates, a Sagian Plate Sealer 18, two Plate Slides 19 for waste plates and tip racks disposal, as Sample Treatment Devices: three LabSystems Multidrop 8-Channel Dispensers 20, a Beckman Biomek 2000 Liquid Handling Robot 21, a Beckman Multimek 96-channel dispenser 22, an Inpeco 20-position vertical Plate Shaker 23, a Heraeus BB 6220 M3 Incubator 24 with sliding back door, a Beckman GS 6R Plate Centrifuge 25 modified by Inpeco for automatic loading, an SLT Columbus Plate Washer 26, and as Sample Assay Devices: a Wallac Trilux 1450-025 Scintillation Counter 27 with ParaLux option, a Wallac Victor2 Multilabel Detector 28, an SLT SpectraIII Colourimetric Plate Reader 29.

In the state of the art, there are multi-robot or multi-module-screening systems in which Samples Containers could easily be handled at a rate of 1 plate every minute. However, to read the plates, for example by radiometric or fluorescence counting, it takes typically 8–12 minutes for each plate. As a consequence, those kind of systems have serious bottleneck problems and plates are normally counted (i.e. assayed) off-line. Actually, plate counting is part of the protocol itself and its capacity should be considered and included when defining the throughput of a screening program.

Not only plate reading, but also other steps may cause bottlenecks in a system, although to a minor extent. Furthermore, small technical problems may occur, that can temporarily slow down or halt the system. If bottlenecks in a protocol cannot be avoided, it could be possible to use a blocking agent to stop for example an enzyme assay. In this way the timing of the rest of the protocol is not critical anymore and the plate may be read after the completion of the steps having time constraints or eventually taken off-line.

Therefore, to increase the throughput of a certain screening format and to prevent bottlenecks beyond a certain limit, it will be necessary to use multiple robots and in some cases multiple instruments or pieces of equipment (e.g. 2 or 3 scintillation counters) and/or off-line processing steps.

Running a huge screening operation with tens of millions of samples in plates per year can easily justify investing in a number of screening systems, each of which may be specialised to perform a particular type of assay, such as cellular (radiometric or fluorescent), enzymatic (including also colourimetric) or other ones. The instruments or equipment that are part of each system do not need to be particularly different one from the other, as normally the same type of experiment is performed routinely. For this reason, the capacity of incubators, stackers, dispensers, washers and even readers can be adjusted to the particular type of screening, which should allow for a high level of optimisation. Alternatively, several screening systems could do essentially the same type of job as a specialised screening system of this type.

The case becomes somewhat different when a smaller screening process has to be run, perhaps not for tens of millions of samples per year, but for 5–10 million samples, with a significant component of concentration-response curves for hit and lead optimisation. Now it may become an investment issue to have several pipetting robots, incubating plate carousels and more costly plate readers for a relatively low throughput per Laboratory workcell, while maintaining the flexibility to respond to the varying needs of the targets and the corresponding assay formats. In this case a single but relatively complex robotic screening workcell, equipped for a wide range of assay types, which can easily be switched from one to another assay type, may be a good solution. Since all pieces of equipment and operations (excluding perhaps the cell plating and compound plate preparation, which are often better and more easily done in separate, specialised laboratories) make part of the workcell, the assay itself should run hands-off up to the plate transport to the waste containers.

As each robotic task may take up to one minute, it is clear that simple assays have a higher steady state throughput than complex assays. Actual robot time may vary from 2 to 7 minutes in most typical screening assays, which allow for a theoretical throughput of 8 to 30 plates per hour using a flexible single-robot system. If the system is operated 8 hours a day, 4 days a week, 40 weeks a year, this allows for screening capacities of 1.0 to 3.9 million samples per year using 96-well plates and even 4 to 15 million samples using the 384-well format.

Static scheduling of screening protocols provides an identical sample history for all plates, although appropriate optimisation of the throughput and the way protocols are executed (the order of operations) is based on the knowledge and the experience of the scientist. Dynamic scheduling systems have several interesting advantages, like the possibility to add plates or other protocols once the workcell has already started the execution, or the possibility to resume the original run automatically after a User intervention or other kinds of interruptions. Dynamic scheduling systems usually are not capable of maintaining requested timing and therefore are only useful for protocols with relaxed timing constraints.

Thanks to the present invention, it is possible to provide a Laboratory Automation Workcell System particularly interesting for medium/high throughput situations where very high flexibility and adaptability are required. In particular, the reactivity of the system gives the possibility to support many different assay formats sequentially or in parallel and immediate adaptability to program changes and unforeseen circumstances around and during a program run.

Moreover, the Laboratory Automation Workcell System according to the present invention, is flexible and thus capable to support any kind of Protocol; the assay implementation is easy and quick to perform; Sample Results are immediately and easily accessible in a standard format; and it is rigorously modular, so that any subsystem might be substituted with an upgraded or completely new module whenever required.

The scheduling process enables the User of the Laboratory Automation Workcell System to define a set of operation steps using the Resources of the system, set the number of Samples Plates to be assayed, generate a feasible program for processing all Samples and execute the program.

The Laboratory Workcell Management System includes a Graphical User Interface (GUI), able to create the Protocols to be stored in the Protocol Database and a Diagnostic Module to troubleshoot eventual problems. The Process Controller acquires the programs to be run, controls the timing with the internal database that maintains the history and status of each plate processed through the system. It communicates with the Resource Drivers, while it creates a log file and data export files for the Laboratory Information System. Finally, the Resource Drivers communicate with the Resources in a modular and concurrent way.

Each plate has a local copy of its Sample Protocol with its associated execution status stored in the Protocol Database. This allows in a simple way to execute multiple Sample Protocols either sequentially or in competition.

Thanks to the RLS and the RPS variables, the Process Controller knows the status of each Resource at any moment. Each Resource can then operate as an independent module in a parallel fashion (multi-threading) with respect to the other Resources of the System. Therefore, a series of logical and physical states are defined, by which the Process Controller can control the system, by means of said Resources.

The RLS has a finite number of logical values that allow the communication between each Resource Driver and the Process Controller. The Process Controller initiates specific activities only when it reads certain values of the RLS and it may set other values to be communicated to the Driver. The Driver can read and write different values and act upon them consequentially. Using the RLS as a means of communication, the Process Controller and the Drivers together can execute Sample Protocols.

The following values of the RLS can be considered as example.

Off: the Process Controller checks whether the Resource is needed for Protocols that have been foreseen, and in case it launches the initiation routine and sets the RLS to Busy.

Ready: the Process Controller, depending on the Resource Physical Status (RPS), explained here below, may either launch a command for execution and set the RLS to Busy, or have the plate unloaded from the equipment and set the RLS to Transport.

Transport: in this case, it is the Resource Driver, in communication with the Sample Carrier Device Driver, to unload the plate and set the RLS to Ready.

Busy: also in this case the Process Controller does not react while the Resource Driver, together with the Sample Carrier Device Driver, is loading the plate and running the executable command requested for that Resource. Once the Resource Driver indicates the completion of the task, the Resource Driver sets the RLS to Task End. In case the Resource Driver indicates an error that cannot be automatically recovered by the Resource Driver itself, it will set the RLS to Error. A particular case occurs in a multi-plate assay, where more than one plate needs to be loaded into a Resource before it can execute its own protocol. In this case, after the arrival of a plate, the Resource Driver, in synchronisation with the Sample Carrier Device Driver, puts its RLS immediately to Ready to allow the loading of a next plate.

Task End: this value of the RLS induces the Process Controller to update the protocol of the analysed plate and to execute the management of the data produced by the plate reader. After this, it sets the Resource Driver to Ready.

Error: the error value of the RLS is indicated to the Operator when the Resource Driver is not able to resolve an error message, sending the appropriate command to the Graphical User Interface (GUI). The Operator has to enter the Diagnostics Module and, on the basis of the specific error code, he/she has to decide either to re-execute the task (perhaps after a manual or low-level software intervention), or to consider it concluded and proceed with the next task. In case of an unrecoverable error, the Operator may eventually decide to abort the program. The Diagnostics Module itself will then execute the appropriate command, adjust the appropriate RLS and/or RPS values and pass the control back to the Process Controller for continuing or aborting of the script of the relevant protocol.

The Sample Carrier Device Driver and the Process Controller need the Resource Physical Status parameters (RPS) to define a reliable plate transfer protocol between the Sample Carrier Device (i.e. the robot, in this case) and the appropriate Resource. In particular, Resources that need to open or close a door or to rotate a plate carousel before they can be loaded, unloaded or commanded to run a protocol, need additional parameters to allow unequivocal communication. These parameters are Free-Space, Full, Open, Closed, Unload and Load, depending on the fact that said Resource has free space for new plates, or it is fall, or it is in open, closed, unload or load status respectively. The process that needs to be controlled in detail is always the unloading of an source Resource and the loading of a destination Resource. This happens with the following sequence.

Unloading: the Process Controller, on the basis of the plate protocol and the Resource RLS, needs to move a plate. It will check whether the destination Resource RLS is Ready and the RPS is Free-Space and whether the source Resource RLS is Ready and RPS is either Free-Space (for multiplate capacity) or Full (for single-plate capacity). If these conditions are satisfied, the Process Controller sends its commands to the destination Resource Driver and to the Sample Carrier Device Driver, while setting the RLS of both Drivers to Busy. The Sample Carrier Device Driver sets the source Resource Driver RPS to Unload, which is acknowledged by the Process Controller changing the RLS to Transport. At this point, the Resource Driver, finding itself logically in Transport and physically in Unload will set the Resource into the condition to receive a plate by rotating the plate carousel, opening the access door and setting the RPS to Open. The robot can now take the plate after which the Sample Carrier Device Driver sets the RPS to Closed. The unload operation is now concluded.

Transport: If a plate is moved for the first time, the barcode is not yet known and will be read first. The plate will also be rotated as necessary, facing the short or long side to the right position for the destination Resource.

Loading: the Sample Carrier Device Driver now sets the destination Resource RPS to Load so that it may execute the task to prepare the Resource for reception and to set the RPS to Open. The robot may now put the plate in place, and afterwards the Sample Carrier Device Driver will set the RPS to Closed.

This way of managing plate transport allows the possibility to use the Resources in the best possible way. For instance, a plate incubator door, that should remain closed as much as possible, will be given the command to open its door only when the robot already has the plate to be loaded in its pincers. This mechanism furthermore allows a very simply management of certain errors. In fact, each RPS or RLS modifications happen only when the previous task has been successfully concluded, preventing the possibility that the robot arm hits a closed door or places a plate into a position which is not ready to receive it.

Once the Process Controller knows the logical and physical states of each Resource, it is possible to execute a protocol. However, since many tasks can take place in parallel, and more than one plate will normally be on the Laboratory workspace simultaneously, it is very probable that two or more tasks will call for robot service at the same time and the Process Controller has to decide which action to execute. Real-time execution of tasks based on immediate execution of interrupts from multiple Resources is therefore an unrealistic aim, as it would need an independent robot and unlimited capacity for each step.

At this point a set of heuristics, rules and parameters is defined, to establish the priority of each plate at any moment in any type of protocol. These priority rules depend largely on the protocol itself, and follow mostly the logic of the biological requirements that the experiment poses on the system. Therefore, the logical states and the priority rules allow the Process Controller and the Sample Carrier Device Driver to operate continuously on the basis of a protocol without a pre-scheduled program.

First of all, the system must follow the first-in-first-out principle to prevent that a plate overruns another one in a multi-plate Resource (typically incubators) or a multi-plate protocol. A particular consequence of this rule is also that plates that have progressed further through the protocol have priority over plates that have just started their protocol. This rule favours Resource unloading over loading and helps preventing queues and freeing up system positions.

A Wait parameter can be introduced by the User by means of the GUI and associated to any Resource that has no bi-directional communication to indicate the end of its process (like multi-plate shakers and virtual incubators i.e. plates waiting at room temperature for the next processing step). The Process Controller will not move plates before the Wait period has passed. The Wait parameter also permits to link two non-consecutive steps. If a plate needs to be read 10 minutes after reagent addition, but there are still a shake step and a plate sealing step in between, it is possible to place the plate into a carousel after the sealing step and to specify a 10 minutes incubation period with respect to the reagent addition step. This allows a very precise control of a reaction and can prevent the use of stop-reagents.

A Critical Timing parameter (a delay) can be introduced by the User by means of the GUI and associated to any Resource. This is a purely biology-driven parameter. If for example an incubation period of cells or membranes in a $CO_2$ incubator must take 45 minutes, but no more than 50 minutes, the robot must complete its current activity and unload the plate from the incubator within the 50 minutes. At the end of the 50 minutes period this operation must have absolute priority and the robot should leave any other activity to allow the Unload operation before continuing the program. Critical Timing may be imposed to every incubation step, including virtual incubations defined by the Wait parameter.

These three rules by themselves are sufficient to define priorities amongst plates. Actually, they are used to define a single priority score, based on expired Wait times and Critical Timing for each plate at each plate motion, which is then used as a simple tool to establish the priority of each plate at any moment in the Laboratory Automation Workcell System.

There are cases in which there is a slow step in the protocol with limited capacity, e.g. reading the plates with a beta-counter, which may require sometimes 10–15 minutes per plate. The Process Controller will always tend to maximise the throughput of the system and initiate the execution of a new plate if there are no other activities with higher priority and the robot is free. As the total robot time for a protocol is often only 5 to 7 minutes, this will cause an overload and a growing waiting list just before the relatively slow beta-counter.

There are two radically different approaches to this problem. The first one is to take the plates off-line for counting or, if timing is not important, to leave the plates on the LAWS for counting them when the beta-counter is free. The second one is to create some feedback mechanism to counteract LAWS overloading. A new concept, the variable Bottleneck, is introduced to deal with the traffic problems. The Bottleneck is caused by a slow Resource (like the beta-counter in our example), but more generally it represents the minimum time that is needed between processing one plate and the next one without causing a traffic jam. The Bottleneck value becomes therefore a crucial parameter that allows the control of plate traffic on a LAWS. Its initial value may be set (in the GUI) to the length of a known slow step (derived during assay optimisation) or simply taking 30–60 seconds for every protocol step, as this is the minimum robot time required in steady state to process each single plate. Three cases can be distinguished to fully control the throughput.

Resources call for transport robot tasks approximately at the same moment and some delays accumulate, without causing a violation of the Critical Delay parameters. Essentially, this means that the transport robot has not enough free time to service all requests. On the basis of the accumulated delay, the Bottleneck value may be gradually increased until no significant delays accumulate. The only effect on the LAWS is that new plates enter with a lower frequency, and delays will gradually decay.

In case of violation of Critical Delay parameters, the system is in an overload condition even if this is normally not immediately recognised as such. At this point, a simple increase of the Bottleneck parameter is not sufficient and new plate entry is completely blocked until the violation of Critical Delay has been managed. At this point the Bottleneck will be recalculated as in the previous case and the plates waiting for admission to the LAWS will be rescheduled accordingly.

The third case consists of no delays at all and the transport robot actually having spare time. In this case the Bottleneck can gradually be shortened, based on the level of spare time of the robot itself.

The resulting system actually provides a negative and a positive feedback loop that can effectively optimise the plate throughput on the LAWS. Giving the Bottleneck a start value close to the real experimental value, the Process Controller may start close to the optimal throughput and only minor corrections are needed. A very regular process will be the result, without any problems that are the consequence of having the transport robot operate at maximum capacity, irrespective of bottlenecks in the protocol.

It can be understood intuitively that constraining the Laboratory Automation Workcell System to very precise timing at multiple steps in a Protocol will induce the system to reduce the frequency with which new plates start their processing as the transport robot will continuously serve critical steps. It is therefore necessary that precise Wait and other timing constraints together with their Critical Timing parameters are used cautiously and with good sense. The less critical the timing of a protocol is, the more flexibility for optimisation the LAWS has, and the higher the throughput will be.

As the overall throughput of an assay includes counting and data analysis steps, it is impossible to process 200 plates per day, while it will take at least 2 days and nights of uninterrupted counting to complete the assay protocol. In that case it may be rather useful to process 70 plates per day including counting and data analysis, using the free processing time of the LAWS to do something else. The only alternative for running this assay at higher throughput would be integrating additional plate counters.

The Graphical User Interface (GUI) has three different functions. The first one is the creation of Sample Protocols, i.e. the definition of a processing path that each plate of a batch may undergo during an experimental run. The second one is the creation and the execution of a batch run program in which all locations of the plates at the start of a run are defined as well as the Protocol that they will be submitted to. Finally, there is a diagnostic module that allows to access most Resources for troubleshooting and to intervene manually in case an unrecoverable error occurred.

The creation or modification of any protocol from the GUI is quite intuitive, fast and can be learnt with minimal training. It basically consists of pointing and clicking, on a map of the LAWS, at the Resources that need to be used in the Protocol. For each Resource a pop-up window appears and it is possible to set a series of parameters specific for that Resource in that Protocol. This parameters include elements like addition of a certain volume of a reagent to all wells or to specific wells on a plate for a dispenser, shaking speed and time for a plate shaker, a read protocol ID for a plate reader, the time a plate needs to remain in an incubator, or any other instruction that the User specifies.

At this point the User can also set the priority rules (see here below) by defining the Critical Timing parameter, e.g. a maximum incubation time, or an optional Bottleneck parameter. It is also possible to create ramified protocols by setting a Node point in the protocol. This allows for instance the transfer of a plate to another position, the introduction of new plates (called daughter plates) and the differentiation of processing of the original and the daughter plates.

While creating the Protocol in this way, a text window is shown in which the script of low-level commands are displayed. It is possible at any moment during the Protocol definition (or when recalling an earlier defined Protocol) to modify, add or delete any line of this script. Protocols are saved, into the protocol Database, with a specific identification and version number so that they can be used in any future moment.

To run the Laboratory Automation Workcell System, the Operator will have to load one or more Protocols and indicate plate types and positions for each Protocol. Like in the Protocol definition phase, simply clicking on the plate carousels (also within an incubator for cellular assays), a plate position pop-up window appears, on which the User can indicate which plate positions are filled and which type of plates or tip racks are used (choosing from an appropriate list of available plates and tip racks). Actually, each Resource Driver has its own small database in which it keeps track of all plates that it is containing or processing at that moment in time. This allows the Process Controller and the Sample Carrier Device Driver to fully control and check the status of each plate as necessary.

At any moment, also during the run of a Protocol, the User can define additional runs and simply add them to the running batch. The system allows either sequential processing, i.e. additional plates will be run at the end of the batch of plates already running (as if some plates had been added to the original protocol), or parallel processing, i.e. the second protocol will run as soon as the LAWS has free processing time available. It will be evident that running in parallel two complex protocols that each could saturate the LAWS will significantly slow down either protocol. Running an easy two-step protocol in the wait times of a complex protocol with long incubation times or a slow plate reading step may be very successful and will allow optimal use of the LAWS.

The GUI has some additional features that help the User in troubleshooting error conditions that may occur.

When no Protocol is being executed, a Maintenance function may be activated to access low-level control of each Resource, including the transport robot. In this way, each Resource can be set to any status desired by the Operator for purposes of maintenance or quality control.

During a run, when the Process Controller indicates that an error, that the system could not recover automatically, has occurred, the Operator may activate the Diagnostics function, interrupt the run and access the low-level control options. In this way he/she can either reset a Resource via software or allow the manual intervention and reset a Resource (e.g. to release a plate blocked in a reader or to adjust the settings of a plate sealer that has missed a plate). Once the error condition has been cancelled, the failed operation may be retried or skipped and the diagnostics mode may be left, allowing the Process Controller to continue processing the batch. The Operator also has the possibility during a run to intervene on Resources, which are not in error condition. This is done through the Maintenance function. Finally, the Operator may at any moment select the Stand-by function to intervene manually in the LAWS. The system will halt the next command and will continue only when the Stand-by status is released by the Operator.

In all these cases, the extreme flexibility of this dynamic and reactive control of the LAWS will recover steady state processing very quickly after any interruption of batch execution. Based on its automatic feedback mechanism, plate entry will be slowed down until the system has recovered its steady state.

Control of data flow in the LAWS is completely based on barcode management. Each screening plate, being 96, 384 or higher well density format, must have a barcode affixed on the left front (short side) or right front (long side) of the plate. The barcode defines the plate contents, which can be retrieved from the Database. During the screening procedure there is no need to retrieve this information. The barcode becomes a mere plate ID, which is assigned to a standardised data export file. In case the compounds cannot be pre-dispensed into the plates but have to be dispensed during the assay (e.g. some agonist-activated assays), the barcode will inherit the plate map of the mother compound plate. The standardised export file contains the data deriving from any plate reader and a number of meta-data that describe the experiment (like date, time, Operator name, protocol name, reader type, reader settings for positive control of e.g. correct settings of filters and measurement units). The data are saved locally, but are continuously accessible through the network by the Laboratory Information System.

Data analysis is performed off-line, and can be done right from the moment the screening execution has completed. As the LAWS and the data analysis software are both based on the barcode and on centralised plate map management, there is no need to maintain a particular plate order while loading the LAWS. Loading 100 or more plates on the plate carousels can consequently be done without the fear of inverting any plate order or location. Also it will be impossible to assign data to the wrong plate, because of mixed plate identification between a reader and the screening system.

Figure 4:
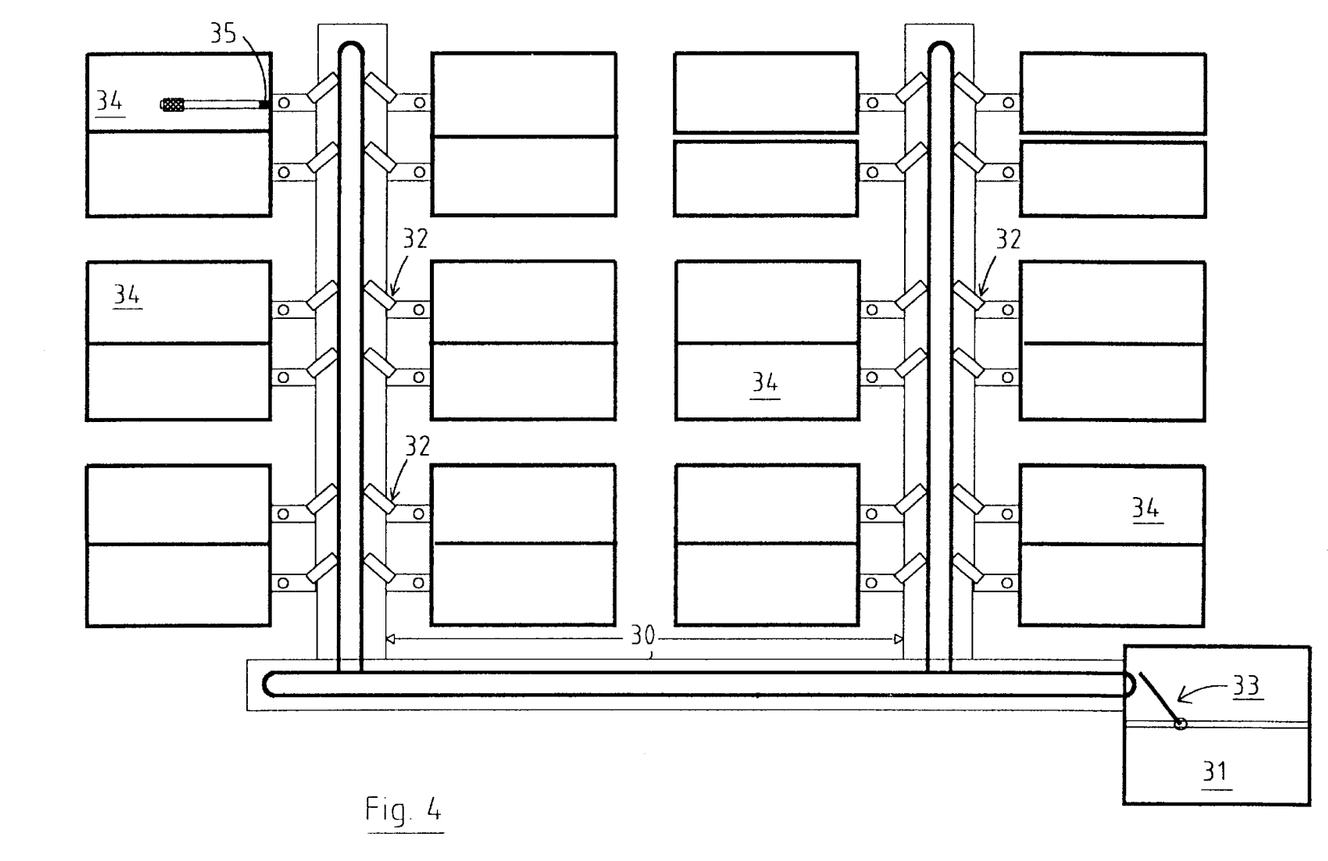
FIG. 4 shows the layout of a Bio-Repository Workcell System.

An Example of Bio-Repository Workcell System that follows the Method of the present invention, shown in FIG. 4, integrates as Sample Containers: sample tubes containing a biological fluid, that has to be kept in refrigerators for a long time and delivered upon request for research analysis, genetic screening or other reasons, and the following pieces of equipment as Resources: Sample Carrier Devices: an Inpeco Transport and Positioning Module (TPM) 30, i.e. a belt conveyor system transporting Pallets (i.e. single sample carriers) containing Sample Tubes (each Pallet is identified by a radio-frequency transponder, appropriately read from time to time by radio frequency devices integrated in a Transponder Tag Reading System), an Input/Output Module (IOM) robot 31 to move samples from/to the Input/Output area to/from the TPM, and one or more transport robot systems 32 capable to move samples into and out from refrigerator systems where the samples are loaded to be stored or unloaded to be assayed, as Sample Container Handling Devices: a barcode reader 33 for sample identification, one or more refrigeration systems 34 (or other storing systems) to store samples, and a barcode reader 35 inside each refrigeration system for Sample Container double-check reading.

The prior art in bio-repositories foresees the manual loading and offloading of samples to and from refrigerators, thus creating problems when the number of samples to be handled is high and introducing risks for the Operators, especially for low ambient temperature in cold chambers or because of liquid nitrogen-based refrigerators.

Also, the manual handling of samples introduces some problems in the management and consistency of the sample database, the possibility of human errors and an inefficient management of the space inside the refrigerators (it is in fact difficult and time consuming to optimise manually the distribution of samples inside those systems).

On the contrary, thanks to the present invention, the Bio-Repository Workcell System that uses the Laboratory Automation Management System, automates all the Bio-Repository tasks, i.e. loading, offloading and compacting samples.

This target is achieved by centralising the sample database in the Workcell System Data Manager, and handling the loading and the offloading of samples into and out from refrigerators in a fully automatic way, allowing the Operator to load samples into an Input/Output area, where samples are automatically recognised, transported and loaded to the proper refrigerator, and to request samples locally from the Graphic User Interface or remotely from the Laboratory Information System, allowing the system to automatically unload the requested samples from the appropriate refrigerators, and transport them to the Input/Output area, re-compacting as necessary the free space generated inside the refrigerators.

The management of this kind of Workcell System is similar to the one described in the above examples, and can be integrated with any Assay Device to perform automatically the requested screening or assaying analyses on the appropriate samples.

In particular, the RLS variable indicate the status of the current task execution of the relevant Resource, i.e. it may be Ready if it is ready to execute new tasks, Busy if it is busy executing a task and cannot currently receive new commands, Error if it is in error state, Task End if it has terminated its current task and it is waiting that the Process Controller updates the RPS variables, etc.

The RPS variables indicate the physical status of a resource, e.g. for a refrigeration system, the RPS is a set of variables indicating the number of samples contained in that Resource, their fragmentation status (for re-compacting options), their accessibility and availability, etc.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. Method for the management of Workcell Systems, using an Automation Management System to control a plurality of Resources, designated to handle a plurality of Samples along said Workcell Systems to perform operations on said Samples, comprising the following steps:

associating a Sample Protocol to each Sample,
   associating to each Resource a Resource Driver, capable to drive said Resource,
   controlling each of said Resource Driver by a Process Controller which communicates with the other Resource Drivers by means of variables associated to each Resource, said variables defining and modifying the status of said Resources,
   executing said Sample Protocols by said Process Controller in a concurrent way to achieve multi-threading, bottleneck avoidance, dynamic assignment of Resources in mutual exclusion, sample priority handling, Resource load balancing and automatic error recovery,
   automatically modifying said Sample Protocols by continuously re-scheduling automatic tasks on different Resources, according to results of the step of executing said Sample Protocols and the status of said Resources as indicated by a status of said variables, such that an intelligent and reactive workflow control process that automatically and dynamically adjusts to resource status is performed.

2. Method according to claim 1 wherein the Workcell System is a Laboratory Automation Workcell System, and each Sample is a biological specimen collected in a Sample Container which includes one or more Samples.

3. Method according to claim 1 wherein said Workcell System includes a Data Manager handling Sample data and Sample Protocols, said Data Manager operating in co-ordination with the other Workcell System Resources by means of a set of variables used for communication.

4. Method according to claim 1 wherein said Workcell System includes a Graphic User Interface for interfacing with a User; said Graphic User Interface operating in co-ordination with the other Workcell System Resources by means of a set of variables indicating the status of the Resources.

5. Method according to claim 1 wherein said Workcell System includes a Laboratory Information System Driver for handling communication with a Laboratory Information System, said Laboratory Information System Driver operating in co-ordination with the other Workcell System Resources by means of a set of variables indicating a status of the Driver.

6. Method according to claim 2 wherein said Workcell System includes as Resources one or more Sample Carrier Devices, designed to move Samples along the Laboratory Automation Workcell System.

7. Method according to claim 1 wherein said Workcell System includes as Resources one or more Sample Treatment Devices for modifying the Samples for required assays.

8. Method according to claim 1 wherein said Workcell System includes as Resources one or more Sample Container Handling Devices, dedicated to dispense, store, dispose or alter properties of a Sample Container.

9. Method according to claim 1 wherein said Workcell System includes as Resources one or more Sample Assay Devices, dedicated to determine a quantity of one or more components in a Sample.

10. Method according to claim 2 wherein the Automation Management System controls and integrates said Resources in order to have a homogeneous and concurrent treatment of Samples along the Workcell System, by associating to each Sample Container a Sample Protocol, and executing all the Sample Protocols in a concurrent way.

11. Method according to claim 2 wherein each Sample Container is associated to an unique identifier and each identifier is associated to a Sample Protocol, whereas said Sample Protocol must be executed on the Sample or the set of Samples contained in the associated Sample Container.

12. Method according to claim 5 wherein the Automation Management System foresees the automatic modification of the Protocols, while they are running, depending on a user request, a Laboratory Information System request or an automatic request.

13. Method according to claim 1 wherein each Sample Protocol is associated to a Priority Level updateable during the execution of said Protocol.

14. Method according to claim 1 wherein each Resource used in a Sample Protocol is associated to a Wait Parameter to indicate a time when the Resource completes its task in that Sample Protocol, and a Critical Time Parameter at completion which the Resource must have absolute priority with respect to any other Protocol.

15. Method according to claim 6 wherein said Laboratory Automation Workcell System is an automated Sample screening or assaying system and wherein said at least one Sample Carrier device is able to transfer a plurality of Sample Containers, each Container including at least one Sample, between said plurality of Resources.

16. Method according to claim 1 wherein said variables used in said step of controlling said Resource Drivers by said Process Controller include Resource Logical Status (RLS), that expresses various logical conditions of associated Resource and Resource Physical Status (RPS), expressing various physical conditions of the associated Resource.

17. Method according to claim 1 wherein the Process Controller, according to the status of the various Resources can automatically decide to re-schedule Sample Protocol activities at any time.

18. Method according to claim 3 wherein the Data Manager, according to the status of Sample Results and expert-system rules taught to the System, is capable to generate automatic requests to modify Sample Protocols or ask for User intervention to treat special and unforeseen cases.

19. Method according to claim 1 dedicated to the control of an In Vitro Diagnostics (IVD) Workcell, that performs sample treatment and test analyses on biological samples using Diagnostics Instruments as Sample Assay Devices.

20. Method according to claim 1 dedicated to the control of a High Throughput Screening (HTS) Laboratory Automation Workcell System, that performs screening analyses of biological samples on Sample Assay Devices following different protocols.

21. Method according to claim 1 dedicated to the control of a Nucleic Acid Technology (NAT) Workcell, having a NAT Laboratory Automation Workcell System that performs sample treatment and test analyses on nucleic acids of biological samples.

22. Method according to claim 1 dedicated to the control of a Bio-Repository Laboratory Automation Workcell System, that is used as a permanent storage for biological samples, that may be kept refrigerated for years, and used upon request.

* * * * *